US009255834B2

(12) United States Patent
    Nissen

(10) Patent No.: US 9,255,834 B2
(45) Date of Patent: Feb. 9, 2016

(54) SYSTEM AND METHOD FOR DETECTING OBJECTS IN A FLUID SYSTEM

(75) Inventor: Jeffrey P. Nissen, Fort Worth, TX (US)

(73) Assignee: Textron Innovations Inc., Providence, RI (US)

(*) Notice: Subject to any disclaimer, the term of this patent is extended or adjusted under 35 U.S.C. 154(b) by 219 days.

(21) Appl. No.: 13/699,861

(22) PCT Filed: Jun. 15, 2011

(86) PCT No.: PCT/US2011/040414
§ 371 (c)(1),
(2), (4) Date: Nov. 26, 2012

(87) PCT Pub. No.: WO2012/173606
PCT Pub. Date: Dec. 20, 2012

(65) Prior Publication Data
US 2013/0160549 A1    Jun. 27, 2013

(51) Int. Cl.
*G01H 1/00* (2006.01)
*G01H 3/00* (2006.01)
*G01N 29/032* (2006.01)
*G01N 29/22* (2006.01)

(52) U.S. Cl.
CPC .............. *G01H 3/00* (2013.01); *G01N 29/032* (2013.01); *G01N 29/222* (2013.01); *G01N 2291/02416* (2013.01); *G01N 2291/044* (2013.01)

(58) Field of Classification Search
CPC ....... G01H 3/00; G01N 29/02; G01N 29/024; G01N 29/032; G01N 29/222
USPC ............. 73/19.03, 61.75, 572, 584, 592, 599, 73/620, 622
See application file for complete search history.

(56) References Cited

U.S. PATENT DOCUMENTS 1,471,547 A  *  10/1923  Chilowsky et al. ............. 367/87
3,575,050 A  *   4/1971  Lynnworth ................ 73/861.27
(Continued)

FOREIGN PATENT DOCUMENTS

DE    20302581 U1    6/2003
JP      8105976 A    4/1996

OTHER PUBLICATIONS

Nobuyuki et al. (English Translation of Japanese Patent Application Publication JP 08-105976).*
(Continued)

*Primary Examiner* — Laura Martin
*Assistant Examiner* — Samir M Shah
(74) *Attorney, Agent, or Firm* — James E. Walton

(57) ABSTRACT

A system is provided in one embodiment for real-time detection of an object in a fluid without interfering with fluid flow. The system may include a sensor element coupled to a fluid passage, which can transmit energy substantially parallel to the flow direction of a fluid in the fluid passage and receive energy reflected from an incident object in the fluid. Reflected energy can also be analyzed as a function of object size and material such that an object can be classified or characterized through appropriate signal analysis. A method is provided in another embodiment for detecting an object in a fluid passage. The method may include transmitting ultrasonic energy through an interface membrane into the fluid and receiving ultrasonic energy reflected from the object. A pressure change in the reflected ultrasonic energy may be measured and converted to a signal for an output device.

18 Claims, 3 Drawing Sheets

(56) References Cited

U.S. PATENT DOCUMENTS

| | | | |
|---|---|---|---|
| 4,237,720 A * | 12/1980 | Abts | 73/61.75 |
| 5,007,291 A * | 4/1991 | Walters et al. | 73/640 |
| 6,193,669 B1 * | 2/2001 | Degany et al. | 600/486 |
| 7,240,553 B2 * | 7/2007 | Segura et al. | 73/597 |
| 7,328,624 B2 * | 2/2008 | Gysling et al. | 73/736 |
| 7,661,293 B2 * | 2/2010 | Dam | 73/19.03 |
| 8,081,069 B2 * | 12/2011 | Haueter et al. | 340/500 |
| 8,800,373 B2 * | 8/2014 | Kleven | 73/644 |
| 2003/0136193 A1 | 7/2003 | Fujimoto | |
| 2004/0011141 A1 * | 1/2004 | Lynnworth | 73/861.27 |
| 2006/0287590 A1 * | 12/2006 | McEowen | 600/331 |
| 2007/0034016 A1 * | 2/2007 | Maginnis et al. | 73/861.28 |
| 2008/0015438 A1 * | 1/2008 | Mehi et al. | 600/447 |
| 2012/0146805 A1 * | 6/2012 | Vick et al. | 340/853.2 |

OTHER PUBLICATIONS

Extended European Search Results dated Aug. 7, 2014 from counterpart EP App. No. 11867695.6.

International Search Report and the Written Opinion of the International Searching Authority mailed by ISA/USA, U.S. Patent and Trademark Office on Oct. 27, 2011 for International Patent Application No. PCT/US2011/040414.

Office Action dated Apr. 27, 2015 from counterpart CA App. No. 2,837,388.

Office Action dated Feb. 16, 2015 from counterpart EP App. No. 11867695.6.

* cited by examiner

SYSTEM AND METHOD FOR DETECTING OBJECTS IN A FLUID SYSTEM

TECHNICAL FIELD

This disclosure relates in general to the field of monitoring fluid systems, and more particularly to a system and method for detecting objects in a fluid system.

DESCRIPTION OF THE PRIOR ART

Modern mechanical systems almost universally include fluid subsystems that interact with bearings and other moving parts to provide lubrication, cooling, and other critical functions. For example, the main bearing and transmission assembly in a helicopter are generally lubricated by a fluid subsystem. Friction and other operational contact can cause the mechanical components deteriorate, though, even with proper lubrication. In extreme cases, this deterioration can lead to failure, which may lead to loss of an aircraft and loss of life if failure occurs in a helicopter, for example.

Fluid in some of these systems can be monitored to detect and measure deterioration of the mechanical systems, such as metallic fragments from the main bearing in a helicopter, and thereby prevent many instances of complete failure. However, these systems generally require particles to accumulate before they can be detected, and thus are not capable of providing real-time detection. Moreover, many modern mechanical systems feature non-metallic materials in lieu of traditional metallic materials. For example, rotorcraft may have high-performance non-metallic transmission components, such as ceramic bearings. Thus, providing real-time detection of debris in fluid systems, particularly non-metallic debris, continues to present significant challenges to engineers and manufacturers.

BRIEF DESCRIPTION OF THE DRAWINGS

The features believed characteristic and novel of the system and method described herein are set forth in the appended claims. However, the system, as well as a preferred mode of use, and further objectives and advantages thereof, will best be understood by reference to the following detailed description when read in conjunction with the accompanying drawings, wherein:

While the system is susceptible to various modifications and alternative forms, novel features thereof are shown and described below through specific example embodiments. It should be understood, however, that the description herein of specific example embodiments is not intended to limit the system or apparatus to the particular forms disclosed, but on the contrary, the intention is to cover all modifications, equivalents, and alternatives falling within the spirit and scope of the appended claims.

DESCRIPTION OF THE PREFERRED EMBODIMENT

Illustrative embodiments of the novel system are described below. In the interest of clarity, not all features of such embodiments may be described. It should be appreciated that in the development of any such system, numerous implementation-specific decisions can be made to achieve specific goals, such as compliance with system-related and business-related constraints, which will vary from one implementation to another. Moreover, it should be appreciated that such decisions might be complex and time-consuming, but would nevertheless be a routine undertaking for those of ordinary skill in the art having the benefit of this disclosure.

In accordance with one embodiment, a system is provided for real-time detection of an object in a fluid without interfering with fluid flow. In a particular example embodiment, the system may include a sensor element coupled to a fluid passage. The sensor element can transmit energy substantially parallel to the flow direction of a fluid in the fluid passage, such as oil in a transmission line. Thus, an incident object (metallic or non-metallic) can reflect energy back to the sensor. The sensor element can measure the reflected energy and convert the measurements pressure waves into a voltage signal, using a piezoelectric element, for example. More particularly, a sensor element may measure pressure changes in the reflected energy and convert the pressure waves into an output signal. In some embodiments, an alarm (e.g., an audible or visual alarm) may be activated, if appropriate. Reflected energy can also be analyzed as a function of object size and material, for example, and thus an object can be classified or characterized (e.g., by size, material type, etc.) through appropriate signal analysis.

Figure 1A:
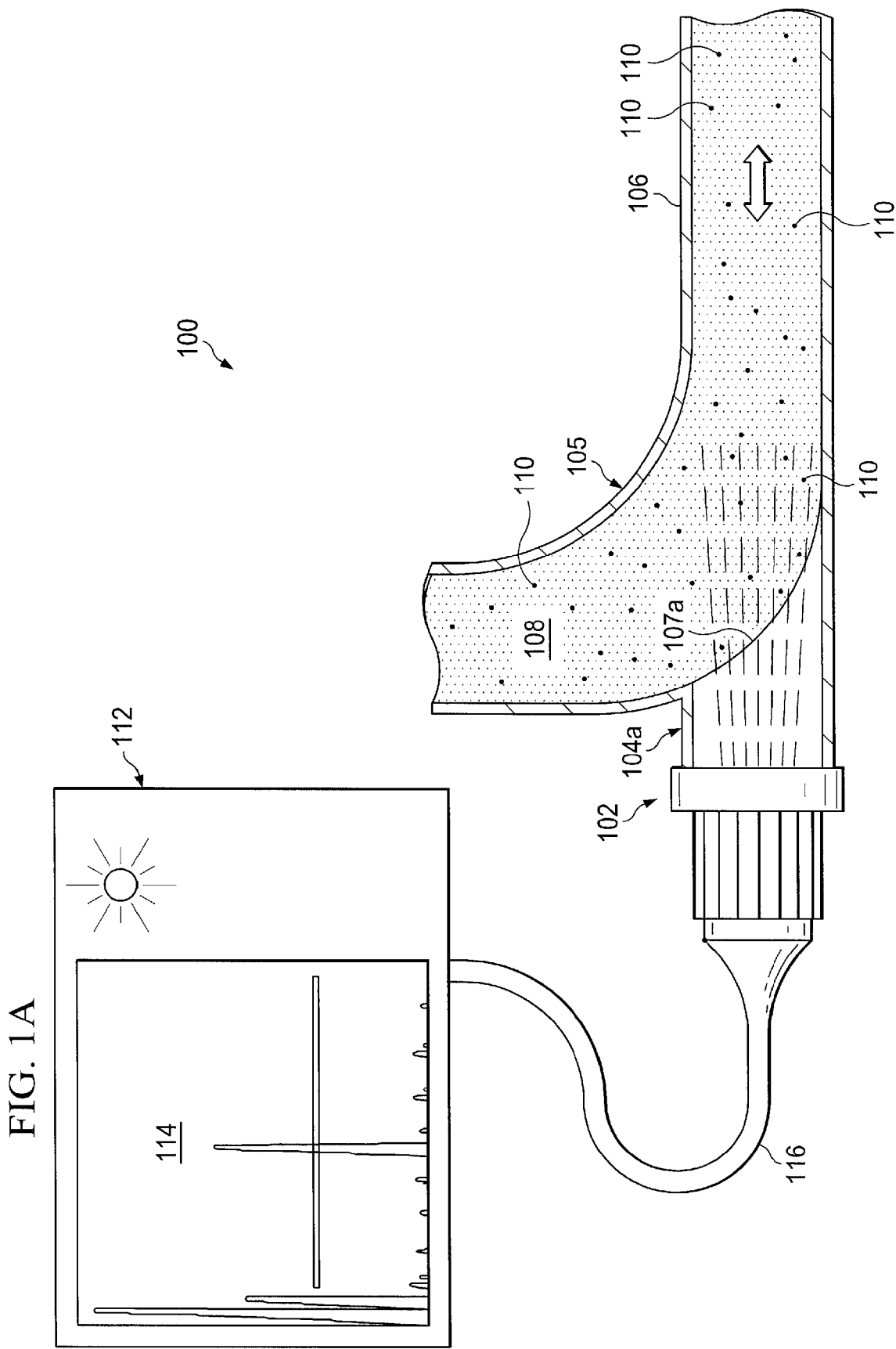
FIG. 1A is a simplified schematic diagram of an example embodiment of a system and method for detecting objects in a fluid, in accordance with this specification.

FIG. 1A is a simplified schematic diagram of an example embodiment of a system 100 for detecting an object in a fluid. FIG. 1 includes a sensor element 102, such as an ultrasonic transducer, coupled to a port 104a. Port 104a may be attached to or integral with a fluid passage 106, such as a steel or titanium conduit. Port 104a is preferably located at a juncture or bend 105 in fluid passage 106, which changes the direction of flow of fluid 108. In operation, sensor element 102 may transmit energy into port 104a through a fluid interface surface 107a into fluid 108. An object 110 may be carried in fluid 108, reflecting energy as it moves toward or away from sensor element 102.

Figure 1B:
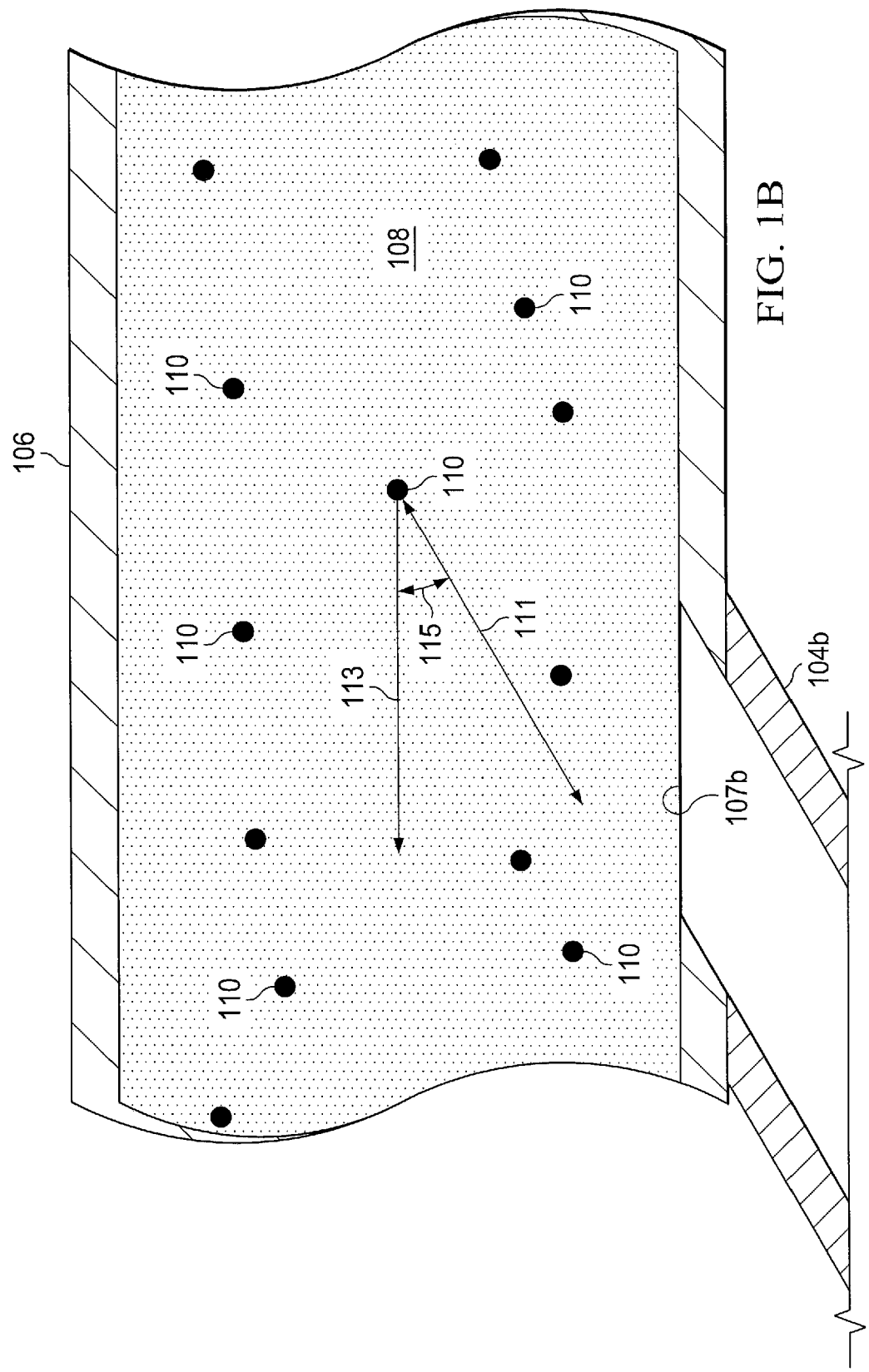
FIG. 1B is a simplified schematic diagram illustrating a potential interaction between an object and energy in another example embodiment of a system and method for detecting objects in a fluid, in accordance with this specification.

FIG. 1B is a simplified schematic diagram illustrating a potential interaction between object 110 and energy 111 in another example embodiment of a system for detecting an object in a fluid. In FIG. 1B, object 110 moves along a path 113 in fluid 108 through fluid passage 106, while energy 111 may be transmitted into port 104b through fluid interface surface 107b into fluid 108. For illustrative purposes, path 113 may be assumed to be parallel to walls of fluid passage 106. As illustrated in FIG. 1B, an angle of incidence 115 between path 113 and energy 111 may vary significantly, such as to accommodate space constraints or retrofitting, for example. Thus, angle of incidence 115 in some embodiments may approach ninety degrees, but is preferably much closer to zero degrees, such that energy 111 is substantially aligned longitudinally with or parallel to path 113, as illustrated in FIG. 1.

Fluid 108 may be any type of fluid, but in certain embodiments, fluid 108 is representative of oil or other fluid commonly used as a lubricant or coolant in a mechanical system, such as a helicopter transmission system. Object 110 is representative of any metallic or non-metallic object, particle, or debris, such as a chip or fragment from a bearing, and may also represent air or other gas bubbles. Sensor element 102 may also be coupled to a processing unit 112 and an output device 114, such as a display screen, audio device, or printer, through a communication link 116, which may be wired or wireless.

In certain embodiments, object 110 may be a fragment of a ceramic bearing in a rotorcraft transmission, for example. Thus, in one example operation, a fragment of a ceramic bearing may be suspended in oil and carried through a transmission line, which may be coupled to an ultrasonic transducer through a port in the transmission line. As the fragment moves toward (or away from) the path of the energy waves transmitted by the ultrasonic transducer, the fragment may reflect energy back to the transducer. The transducer can receive the reflected energy and convert it to an electrical signal, which may then be transmitted to processing unit 112 for further signal analysis.

Figure 2:
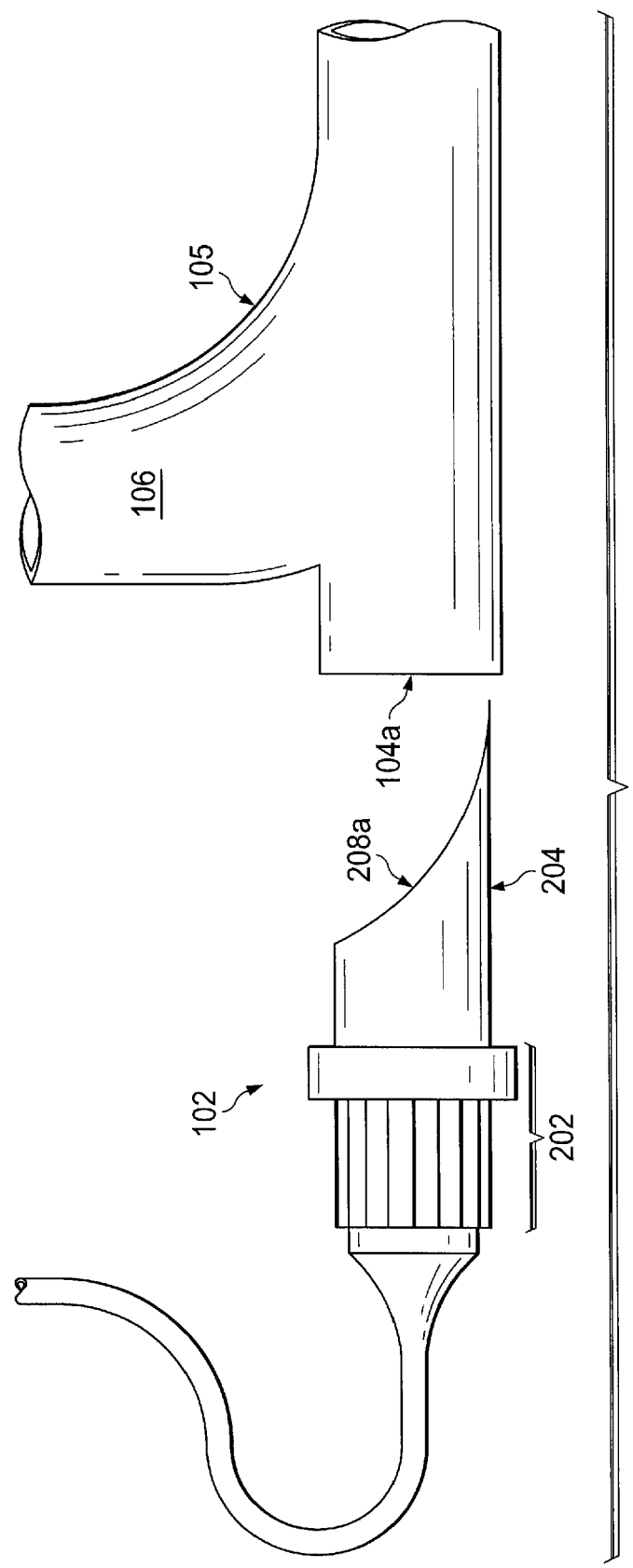
FIG. 2 is a simplified schematic diagram of an exploded partial view of the example embodiment of FIG. 1.

FIG. 2 is a simplified schematic diagram of an exploded partial view of system 100. As shown, sensor element 102 may include a probe element 202 and a fluid interface membrane 204. Interface membrane 204 may be bonded, fused, joined, linked, or otherwise coupled with probe 202 in certain embodiments, and is preferably constructed of a material that substantially matches the acoustic properties of fluid 108. For example, in some applications, interface membrane 204 may preferably be plastic, Aqualine, or Lucite. Fluid port 104a of fluid passage 106 is adapted to receive interface membrane 204, preferably at juncture or bend 105 in fluid passage 106. Interface membrane 204 may further includes a fluid interface surface 208, which in certain embodiments may have a radius of curvature that is substantially similar to the radius of curvature of the bend 105 to maintain substantially laminar flow of fluid 108 through fluid passage 106.

Processing unit 112 may include appropriate hardware that is capable of accepting, performing logic operations on, storing, or displaying data, such as a processor and a memory element. A memory element is inclusive of any volatile or persistent medium in which data, algorithms, and instructions can be stored for any duration, such as a magnetic disk, optical disk, random access memory (RAM), read-only memory (ROM), flash memory, field programmable gate array (FGPA), or an application-specific integrated circuit (ASIC). In some embodiments, a memory element may encompass and be distributed across a plurality of media. Processing unit 112 may also include suitable instructions, algorithms, or other logic elements to facilitate operations described herein. In certain embodiments, these logic elements may be stored in a memory element and retrieved by a processor for execution. Data being measured, tracked, or transformed may be provided or stored in a memory element, including any database, register, table, cache, queue, or other storage structure based on particular needs and implementations, all of which could be referenced in any suitable timeframe.

For example, a processor may be provided that is operable to execute instructions for controlling sensor element 102, measuring energy reflected back to sensor element 102, and converting the reflected energy into a signal suitable for output device 114, such as response display screen. In certain embodiments, a processor may cause probe element 202 to transmit ultrasonic energy through interface membrane 204 into a fluid and measure a pressure change in reflected energy from an object in the fluid. Reflected energy may be converted into a signal representative of a numerical value in a given size scale, for example. In yet other example embodiments, processing unit 112 may be calibrated to trigger an audible or visual alert signal if a measurement indicates a particle size exceeds a certain tolerance limit.

The systems and methods described herein can provide significant advantages, some of which have already been mentioned. For example, such systems and methods can be provided in a lightweight sensor package with a high signal-to-noise ratio and low false detection rate. Moreover, such systems and methods are capable of providing real-time, high-speed detection capability, which may be particularly advantageous in environments with high oil flow rates, such as in aircraft operation.

Certain example embodiments have been shown in the drawings and described above, but variations in these embodiments will be apparent to those skilled in the art. The principles disclosed herein are readily applicable to a variety of systems, including fixed-wing aircraft, rotorcraft, and spacecraft, for example. More particularly, such systems and methods as described herein may be applicable to rotorcraft transmission components using non-metallic bearing components. Moreover, may be applicable to monitoring fluid (e.g., oil, fuel, water) quality and detection of metallic and non-metallic debris in a number of other industries, including heavy machinery, or automotive industries.

The preceding description is for illustration purposes only, and the claims below should not be construed as limited to the specific embodiments shown and described.

The invention claimed is:

1. A method for detecting an object in a fluid in a fluid passage, comprising:
    channeling the fluid around a bend within the fluid passage, the bend having a radius of curvature;
    providing an interface membrane, the interface membrane having a curvature to match the radius of curvature of the bend, the interface membrane being configured to channel the fluid around the radius of curvature;
    coupling an ultrasonic transducer to the fluid passage;
    aligning the ultrasonic transducer such that the ultrasonic transducer transmits ultrasonic energy in a longitudinal direction relative to a flow path of the fluid passing through the fluid passage around the bend;
    transmitting ultrasonic energy through the interface membrane into the fluid at a longitudinal direction relative to the flow path;
    receiving ultrasonic energy reflected from the object;
    measuring a pressure change in the reflected ultrasonic energy; and
    converting the pressure change to a signal to an output device.

2. The method of claim 1, wherein the interface membrane substantially matches acoustic properties of the fluid.

3. The method of claim 1, wherein the interface membrane includes a fluid interface surface adapted to maintain a substantially laminar flow of fluid through the fluid passage.

4. The method of claim 1, further comprising classifying the object based on the pressure change.

5. The method of claim 1, wherein:
    the fluid is flowing through the fluid passage;
    the interface membrane substantially matches acoustic properties of the fluid; and
    the interface membrane includes a fluid interface surface adapted to maintain a substantially laminar flow of fluid through the fluid passage.

6. An apparatus for detecting an object in a fluid in a fluid passage having a bend with a radius of curvature, comprising:
    an interface membrane having a curvature to match the radius of curvature of the bend, the interface membrane being configured to channel the fluid around the radius of curvature;
    an ultrasonic transducer for transmitting energy through the interface membrane into the fluid flowing through the fluid passage and receiving reflected energy from an object in the fluid, the ultrasonic transducer being longitudinally aligned to the fluid passage such that the ultrasonic transducer transmits ultrasonic energy in a longitudinal direction relative to a flow path of the fluid leaving the bend; and a processing unit coupled to the ultrasonic transducer, the processing unit comprising a processor operable to execute instructions for measuring the energy reflected from the object and converting the reflected energy to an output signal;

wherein the interface membrane comprises a fluid interface surface adapted to maintain a substantially laminar flow of fluid through a fluid passage.

7. The apparatus of claim 6, wherein the interface membrane is comprised of a material that substantially matches acoustic properties of the fluid.

8. The apparatus of claim 6, wherein the fluid interface surface is a curved surface.

9. The apparatus of claim 6, wherein the processor is further operable to execute instructions for classifying the object based on the reflected energy.

10. The apparatus of claim 6, wherein the processor measures a pressure change in reflected energy.

11. The apparatus of claim 6, wherein the object is a non-metallic object.

12. An apparatus, comprising:
a fluid passage having a port and a bend with a radius of curvature;
an interface membrane having a curvature to match the radius of curvature of the bend, the interface membrane being configured to channel the fluid around the radius of curvature;
a sensor element coupled to the port for transmitting energy into a fluid flowing through the fluid passage and receiving reflected energy from an object in the fluid, without interfering with the fluid flowing through the fluid passage, the sensor having:
an ultrasonic transducer longitudinally aligned to the fluid passage such that the ultrasonic transducer transmits ultrasonic energy in a longitudinal direction relative to a flow path of the fluid leaving the bend; and
a processing unit coupled to the sensor element, the processing unit comprising a processor operable to execute instructions for measuring the energy reflected from the object and converting the reflected energy to an output signal.

13. The apparatus of claim 12, wherein the sensor element comprises:
a probe element for transmitting and receiving the energy; and
an interface membrane coupled to the probe element and received in the port.

14. The apparatus of claim 12, wherein the sensor element comprises:
a probe element for transmitting and receiving the energy; and
an interface membrane coupled to the probe element and received in the port;
wherein the interface membrane is adapted to maintain a substantially laminar flow of fluid through the fluid passage.

15. The apparatus of claim 12, wherein the probe element is an ultrasonic transducer.

16. The apparatus of claim 12, wherein the sensor element comprises:
a probe element for transmitting and receiving the energy; and
an interface membrane coupled to the probe element and received in the port;
wherein the interface membrane substantially matches acoustic properties of the fluid.

17. The apparatus of claim 12, wherein the sensor element comprises:
a probe element for transmitting and receiving the energy; and
an interface membrane coupled to the probe element and received in the port;
wherein the interface membrane comprises a curved fluid interface adapted to maintain a substantially laminar flow of fluid through the fluid passage.

18. The apparatus of claim 12, wherein:
the port is located at a bend in the fluid passage;
the object is a non-metallic object;
the sensor element comprises:
an interface membrane received in the port, wherein the interface membrane substantially matches acoustic properties of the fluid and has a curved fluid interface adapted to maintain a substantially laminar flow of fluid through the fluid passage; and
the processor is further operable to execute instructions for classifying the object based on the reflected energy.

* * * * *